US006488627B1

(12) United States Patent
Kim

(10) Patent No.: US 6,488,627 B1
(45) Date of Patent: Dec. 3, 2002

(54) ULTRASONIC IMAGE SEARCHING APPARATUS AND ULTRASONIC IMAGE TRANSMISSION AND RECEPTION SYSTEM ADOPTING THE SAME

(75) Inventor: Sang Hyun Kim, Seoul (KR)

(73) Assignee: Medison Co., Ltd. (KR)

( * ) Notice: Subject to any disclaimer, the term of this patent is extended or adjusted under 35 U.S.C. 154(b) by 0 days.

(21) Appl. No.: 09/621,924

(22) Filed: Jul. 24, 2000

(30) Foreign Application Priority Data

Nov. 26, 1999 (KR) ............................................. 99-52913

(51) Int. Cl.[7] ................................................. A61B 8/00
(52) U.S. Cl. ....................................................... 600/437
(58) Field of Search ................................. 600/437, 443; 382/128; 709/217–219, 230; 707/316

(56) References Cited

U.S. PATENT DOCUMENTS 5,899,999 A * 5/1999 De Bonet .................... 600/443
5,997,478 A * 12/1999 Jackson et al. .............. 600/437
6,032,678 A * 3/2000 Rottem ........................ 600/437
2001/0043729 A1 * 11/2001 Giger et al. ................. 382/128

* cited by examiner

Primary Examiner—Francis J. Jaworski
(74) Attorney, Agent, or Firm—Bourque & Associates P.A.

(57) ABSTRACT

An ultrasonic image searching apparatus is provided, which includes an input unit for inputting a key word for selecting an object to be searched and an ultrasonic image, a feature extraction unit for extracting the feature of the ultrasonic image inputted via the input unit, a storage unit for storing a plurality of previously acquired ultrasonic images and a database of commentary information and image feature information with respect to each ultrasonic image, a display, and a controller for comparing the key word input from the input unit or the feature extracted from the feature extraction unit with the commentary information and the image feature information in the storage unit and outputting the ultrasonic images contained in the storage unit on the display according to a degree of similarity. Thus, a massive amount of the prestored ultrasonic images can be efficiently searched, and connection with the network such as a web server provides an effect of searching the ultrasonic image.

18 Claims, 3 Drawing Sheets

ULTRASONIC IMAGE SEARCHING APPARATUS AND ULTRASONIC IMAGE TRANSMISSION AND RECEPTION SYSTEM ADOPTING THE SAME

BACKGROUND OF THE INVENTION

1. Field of the Invention

The present invention relates to an ultrasonic image diagnostic system, and more particularly, to an ultrasonic image searching apparatus and an ultrasonic image transmission and reception system adopting the same, in which an ultrasonic image to be desired by a user is searched among ultrasonic images prestored in an ultrasonic image diagnostic system, and the searched results are displayed in order similar to the desired ultrasonic image.

2. Description of the Related Art

According to development of the electronic engineering field, a number of changes have occurred in an ultrasonic image technological field. Among them, a representative one is to process and store images in digital form. Thus, since ultrasonic images are processed digitally, the ultrasonic diagnostic system can process and store an enormous amount of ultrasonic images. A research for searching a desired image among the enormous amount of the stored ultrasonic images is briskly under progress. In particular, in the MPEG (Moving Pictures Expert Group) standard for a moving image compression method, an image searching method for searching a particular image among successive frames is being under studied. Also, in the medical imaging field, a method for searching an image using a frequency conversion method with respect to MRI images, is being researched.

However, most of the existing image searching methods of which the objects are general images in the world of nature, are applied chiefly to personal computers. The existing image searching methods have been applied only to the case where directionality of images is fixed at the time of searching medical images. Thus, there has been no ultrasonic image searching system which is applicable to the ultrasonic image diagnostic system where position of a probe is adjusted to obtain an ultrasonic image.

SUMMARY OF THE INVENTION

To solve the above problems, it is an object of the present invention to provide an ultrasonic image searching apparatus for effectively searching an ultrasonic image.

It is another object of the present invention to provide an ultrasonic image transmission and reception system for searching an ultrasonic image including an ultrasonic image searching apparatus which is connected to a network such as a web server.

To accomplish the above object of the present invention, there is provided an ultrasonic image searching apparatus comprising: an input unit for inputting a key word and an ultrasonic image for selecting an object to be searched; a feature extraction unit for extracting the feature of the ultrasonic image inputted via the input unit; a storage unit for storing a plurality of previously acquired ultrasonic images and a database of commentary information and image feature information with respect to each ultrasonic image; a display; and a controller for comparing the key word input from the input unit or the feature extracted from the feature extraction unit with the commentary information and the image feature information in the storage unit and outputting the ultrasonic images contained in the storage unit on the display according to a degree of similarity.

There is also provided an ultrasonic image transmission and reception system according to the present invention, comprising: a requester for requesting an ultrasonic image to be searched; and a provider connected to the requester on a network, for constructing a separate database storing ultrasonic images, searching an ultrasonic image which has been requested from the requester, and providing the searched result.

BRIEF DESCRIPTION OF THE DRAWINGS

The above objects and other advantages of the present invention will become more apparent by describing the preferred embodiments thereof in more detail with reference to the accompanying drawings in which.

DETAILED DESCRIPTION OF THE PREFERRED EMBODIMENTS

A preferred embodiment of the present invention will be described with reference to the accompanying drawings.

Figure 1:
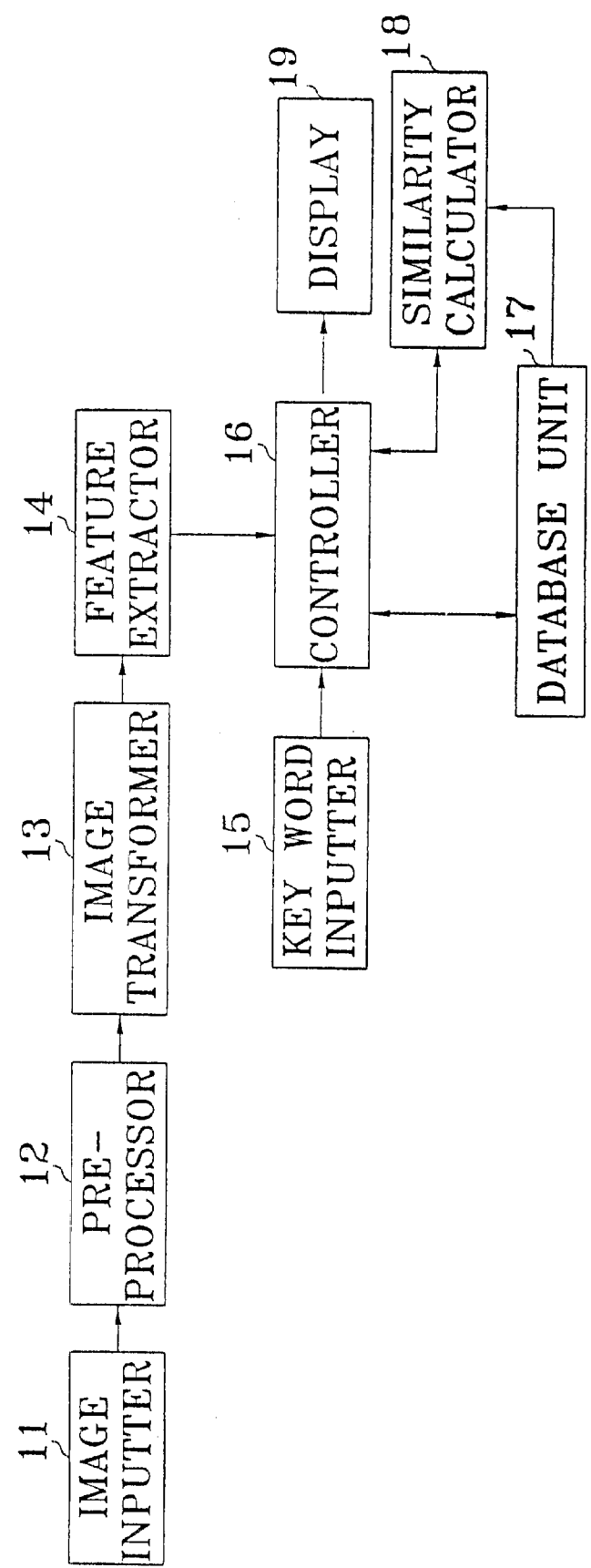
FIG. 1 is a block diagram showing an ultrasonic image searching apparatus according to an embodiment of the present invention.

Referring to FIG. 1, an ultrasonic image searching apparatus according to an embodiment of the present invention includes an image inputter 11 for inputting an ultrasonic image and a key word inputter 15 for inputting a key word. Also, the FIG. 1 apparatus includes a pre-processor 12 for pre-processing the ultrasonic image input from the image inputter 11, an image transformer 13 for image-transforming the pre-processed ultrasonic image, and a feature extractor 14 for extracting the features of the image-transformed ultrasonic image. A controller 16 connected to the output end of the feature extractor 14 is connected to the key word inputter 15 to receive the input key word. Here, the key word can be in the form of both characters and sounds. Hereinafter, characters are input as key words, by way of an example. Also, the controller 16 is connected to a database unit 17 and a similarity calculator 18 in order to transmit and receive signals mutually, and is connected to a display 19 in order to display the images thereon.

Figure 2:
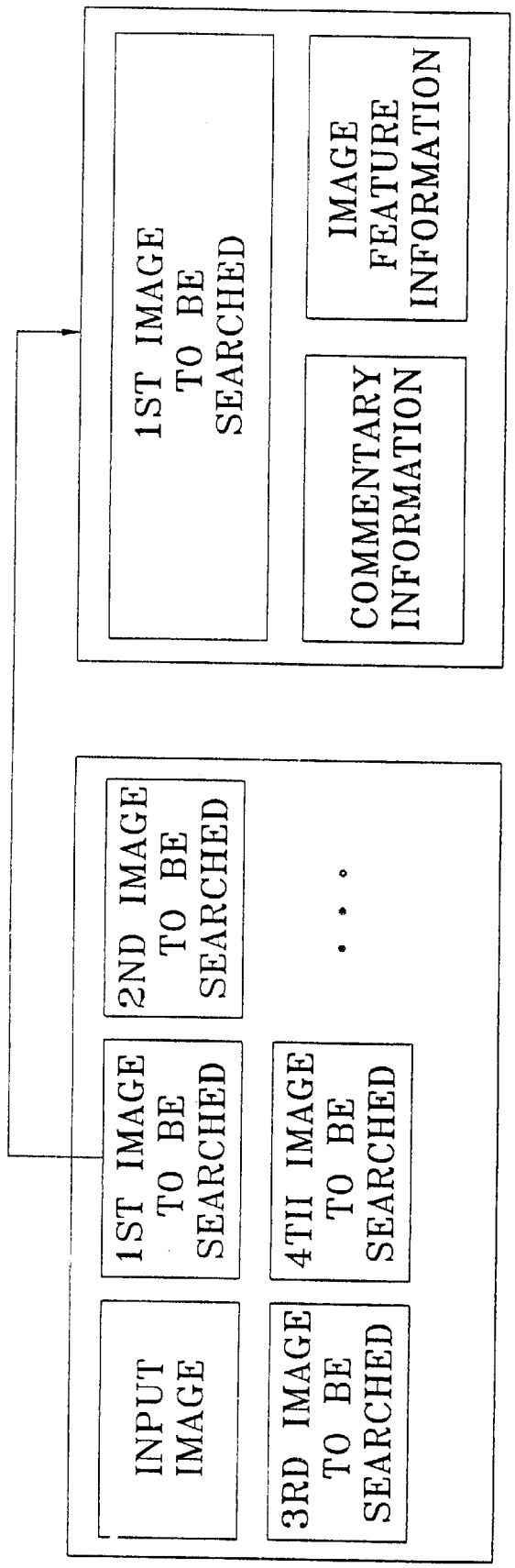
FIG. 2 shows an exemplary screen state illustrating the ultrasonic image searching results of the FIG. 1 apparatus.

The operation of the FIG. 1 ultrasonic image searching apparatus having the above configuration will be described with reference to FIG. 2.

In FIG. 1, a user inputs an image or a key word, to thereby search a desired ultrasonic image. That is. the user inputs characters via the key matrix of the key word inputter 15, or inputs the ultrasonic image via the image inputter 11, to thereby search a desired image. In order to search a desired ultrasonic image from the input image or the key word, the database unit 17 stores commentary information and image feature information which are image information corresponding to each ultrasonic image, as well as pre-stored ultrasonic images. Here, the commentary information is for searching an. image in the case that a user inputs a key word. Also, the image feature information is for searching an image in the case that a user inputs an image, that is, statistical information such as signal distribution of images or a histogram of frequence components.

The two cases for inputting characters or images in order to search a user desired ultrasonic image will be described in more detail.

First, in the case of image searching according to character inputs, a user inputs a key word using the key matrix of the key word inputter 15. When a key word signal for image searching is input to the controller 16, the controller 16 outputs the key word signal to the similarity calculator 18. Also, the controller 16 controls image information corresponding to the pre-stored ultrasonic image of the database unit 17 to be output to the similarity calculator 18. The similarity calculator 18 compares the key word signal input from the controller 16 with the commentary information among the image information output from the database unit 17, to thereby output a degree of similarity to the controller 16. The controller 16 reads out the ultrasonic image having a degree of similarity input from the similarity calculator 18 from the database unit 17. The controller 16 outputs the ultrasonic images read out from the database unit 17 in order of a higher degree of similarity. The display 19 displays the image signal input from the controller 16 thereon as shown in FIG. 2. That is, the searched images are output in order of a higher degree of similarity. In the case that a first searched image is selected, the corresponding image is displayed together with the commentary information and the image feature information.

Secondly, in the case that image searching is performed using an ultrasonic image, the user inputs the ultrasonic image which is currently ultrasonic-scanned using a probe. The image inputter 11 outputs the ultrasonic image signal from the probe to the pre-processor 12. The pre-processor 12 makes the brightness and the contrast of the ultrasonic image from the image inputter 11 equal to those of the ultrasonic image prestored in the database unit 17. and performs pre-processing operations such as noise cancellation of the ultrasonic image signal and sorting of the significant portions in the ultrasonic image. The image transformer 13 receives the pre-processed ultrasonic image signal from the pre-processor 12, and image-transforms it so that feature extraction of the ultrasonic image signal is facilitated. That is, the image transformer 13 transforms the pre-processed ultrasonic image from a spatial region to a frequency region, and classifies the frequency components contained in the ultrasonic image systematically to then output the result. Here, the image transforming method can employ a Wavelet transform, a discrete cosine transform (DCT), and so on. The feature extractor 14 extracts the features of the ultrasonic image from the image transformed ultrasonic image signal input from the image transformer 13. That is, the feature extractor 14 receives the frequency components output from the image transformer 13 and makes them into a histogram to extract the features. Besides, features can be extracted using signal distribution and pattern and motion vector information in the transform region and spatial region. The feature extractor 14 outputs the histogram information of the frequency components in the ultrasonic image signal to the controller 16. The controller 16 receives the histogram information and outputs it to the similarity calculator 18. Also, the controller 16 controls the image information of the prestored ultrasonic images in the database unit 17 so as to be output to the similarity calculator 18. The similarity calculator 18 compares the histogram information input from the controller 16 with that of the prestored ultrasonic images in the database unit 17 and outputs the obtained similarity to the controller 16. The controller 16 reads out from the database unit 17 the ultrasonic images having the similarity output from the similarity calculator 18. The controller 16 outputs the ultrasonic images read out from the database unit 17 in order of a higher similarity. The display 19 displays the image signal input from the controller 16 on a screen as shown in FIG. 2. Here, in the case that diagnostic information is stored together in the database unit 17, the diagnostic information can be also displayed on the screen together with a plurality of searched resultant image. That is, the searched image is output in order of the higher similarity. When a first searched image is selected, the corresponding image is displayed together with the commentary information and the image feature information.

Figure 3:
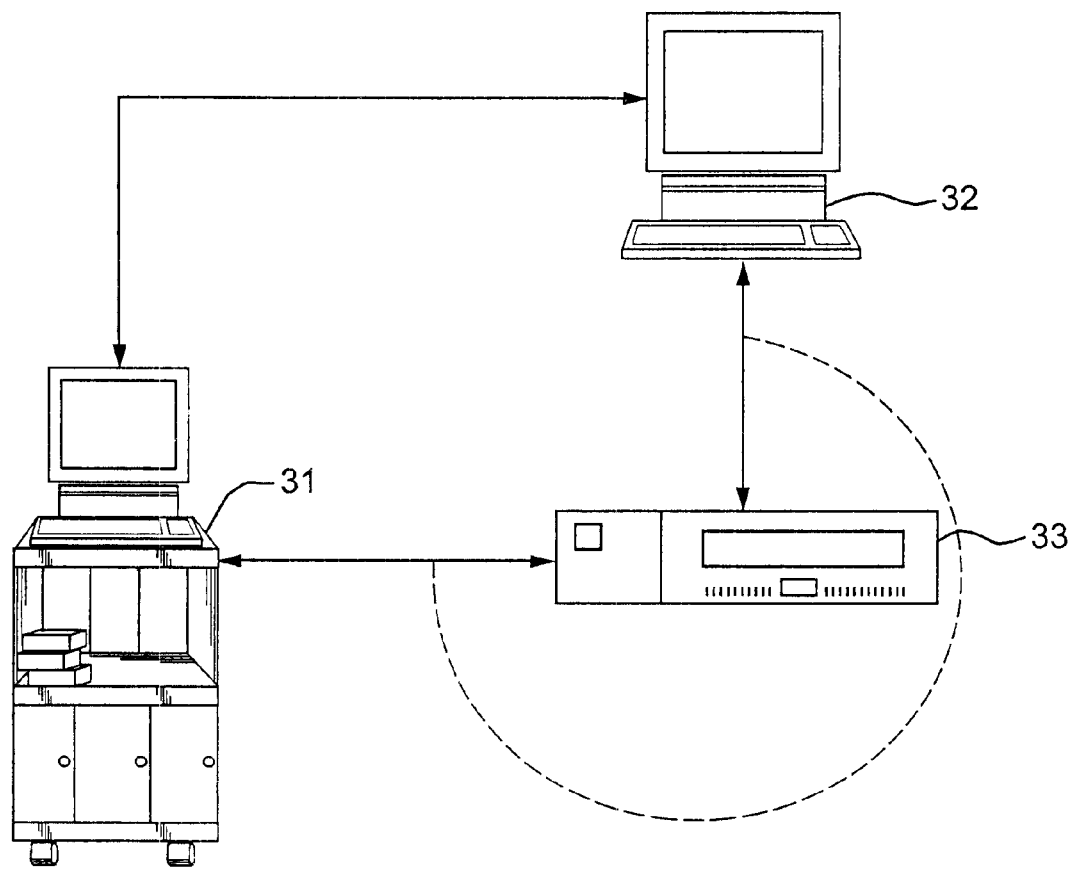
FIG. 3 shows an application on the web Internet in which the ultrasonic image searching apparatus of FIG. 1 is connected to a personal computer (PC).

Also, the above-described ultrasonic image searching apparatus is independently used in the ultrasonic image diagnostic system, and connected on the web via the network, to thereby enable image searching, as well. These are shown in FIG. 3. In the FIG. 3 apparatus, a web server 33 is coupled to an ultrasonic image searching apparatus 31 and a PC 32, to thus receive and transmit the data for searching an ultrasonic image and the searched resultant image, mutually. The web server 33 constructs a database prestoring the ultrasonic images to be searched. Thus, the web server 33 receives a request of a desired ultrasonic image from the ultrasonic image searching apparatus 31 and the PC 32, and finds out the requested ultrasonic image among the prestored ultrasonic images, to then transmit the searched result in order of similarity. Also, the present invention enables an ultrasonic image searching among a plurality of ultrasonic image searching apparatuses which are connected to the Internet or Intranet. Further, a PC is connected to a plurality of ultrasonic image searching apparatuses, to thereby enable an ultrasonic image requested by the PC to be searched in the plurality of ultrasonic image searching apparatuses to then be transmitted.

In the above-described embodiment, the image transformer 13 has been used for extracting the features through an image transformation in order to extract the features of the ultrasonic image. As another embodiment of the present invention, the image transformer 13 can be replaced by an image emphasizer (not shown), to perform the same function. Referring to FIG. 1, the image emphasizer (not shown) is coupled between the pre-processor 12 and the feature extractor 14, instead of the image transformer 13. The image emphasizer (not shown) receives the pre-processed ultrasonic image from the pre-processor 12, and emphasizes the feature of the image in the spatial region via image division or contour extraction, to then output the emphasized ultrasonic image. Then, the feature extractor 14 receives the image emphasized ultrasonic image from the image emphasizer and extracts the feature of the ultrasonic image. The image searching process is same as that of the FIG. 1 description.

The ultrasonic images applied to the above-described embodiments can be two-dimensional ultrasonic images, three-dimensional ultrasonic images, and four-dimensional ultrasonic images.

Also, the above-described embodiment has been described with respect to the cases that the key word is input and the ultrasonic image is input to select an object to be searched, respectively. However, the key word and the ultrasonic image can be simultaneously received, to thereby enable both the commentary information and the image feature information to be searched together, and combine two similarities to complementarily search the ultrasonic image. That is, sum of the similarity of the commentary information and that of the image feature information is used to search the ultrasonic image.

Thus, the present invention can efficiently search a massive amount of the prestored ultrasonic images, and provides an effect of searching the ultrasonic image through connection with the network such as a web server.

What is claimed is:

1. An ultrasonic image searching apparatus comprising:
   an input unit for inputting a key word and an ultrasonic image for selecting an object to be searched;
   a feature extraction unit for extracting at least one feature of said ultrasonic image inputted via said input unit, said feature extraction unit comprising:
   a pre-processor for manipulating at least one quality of said input ultrasonic image;
   an image transformer connected to said pre-processor, said image transformer transforming said preprocessed ultrasonic image from a spatial region to a frequency region having frequency components and classifying said frequency components contained in said ultrasonic image; and
   a feature extractor connected to said image transformer, said feature extractor receiving said frequency components and extracting said features of said ultrasonic image by creating a histogram;
   a storage unit for storing a plurality of previously acquired ultrasonic images and a database of commentary information and image feature information with respect to each ultrasonic image;
   a display; and
   a controller for comparing said key word input from said input unit or said feature extracted from said feature extraction unit with said commentary information and said image feature information in storage unit and outputting said ultrasonic images contained in said storage unit on said display according to degree of similarity.

2. The ultrasonic image searching apparatus according to claim 1, wherein said input unit comprises:
   a key word inputter for inputting a key word of an image to be searched in the form of characters and sounds; and
   an image inputter for inputting an ultrasonic image.

3. The ultrasonic image searching apparatus according to claim 1, wherein said feature extraction unit extracts image feature information in correspondence to that of the pre-stored ultrasonic image.

4. The ultrasonic image searching apparatus according to claim 3, wherein said controller compares the key word input with the commentary information, if the key word has been input from said inputter and compares the ultrasonic image with the image feature information if the ultrasonic image has been input therefrom, to thereby calculate a degree of similarity.

5. The ultrasonic image searching apparatus according to claim 6, wherein said controller comprises:
   a similarity calculator for calculating a degree of similarity by comparing the input key word and ultrasonic image with the commentary information and the image feature information; and
   a controller for controlling the ultrasonic images to be output in order of similarity input from said similarity calculator.

6. The ultrasonic image searching apparatus according to claim 3, wherein said controller compares the key word input from said inputter with the commentary information, and compares the ultrasonic image with the image feature information respectively, to thereby calculate a degree of similarity based on the comparison results.

7. The ultrasonic image searching for apparatus according to claim 6, wherein said controller comprises:
   a similarity calculator for calculating a degree of similarity by comparing the input key word and ultrasonic image with the commentary information and the image feature information; and
   a controller for controlling the ultrasonic images to be output in order of similarity input from said similarity calculator.

8. The ultrasonic image searching apparatus according to claim 1, wherein said feature extraction unit comprises:
   a pre-processor for pre-processing the input ultrasonic image so as to be equal to the conditions of the ultrasonic images prestored in said storage unit;
   an image emphasizer for receiving the pre-processed ultrasonic image from said pre-processor and image-emphasizing the input pre-processed ultrasonic image; and
   a feature extractor for extracting the feature of the ultrasonic image based on the image-emphasized ultrasonic image signal.

9. The ultrasonic image searching apparatus according to claim 1, wherein said controller for controlling an ultrasonic image selected among a plurailty of ultrasonic images displayed on the display so as to be displayed together with the commentary information and the image feature information.

10. The ultrasonic searching apparatus according to claim 1, wherein said object to be searched is a two-dimensional, or four-dimensional ultrasonic image.

11. The ultrasonic image searching apparatus as claimed in claim 1 wherein said image transformer uses a Wavelet transform.

12. The ultrasonic image searching apparatus as claimed in claim 1 wherein said image transformer uses a discrete cosine transform.

13. The ultrasonic image searching apparatus as claimed in claim 1 wherein said feature extractor extracts said features using signal distribution and pattern and motion vector.

14. The ultrasonic image searching apparatus as claimed in claim 1 wherein said storage unit comprises a server.

15. The ultrasonic image searching apparatus as claimed in claim 1 wherein said storage unit comprises a personal computer.

16. The ultrasonic image searching apparatus as claimed in claim 1 wherein said storage unit comprises a plurality of ultrasonic image searching apparatuses.

17. The ultrasonic image searching apparatus as claimed in claim 1 wherein said pre-processor manipulates said at least one quality of said input ultrasonic image using noise cancellation techniques.

18. The ultrasonic image searching apparatus as claimed in claim 1 wherein said pre-processor manipulates said at least one quality of said input ultrasonic image adjusts the brightness and contrast of said input ultrasonic image to approximate the brightness and contrast of said plurality of previously acquired ultrasonic images.

* * * * *